United States Patent [19]

DeMartino et al.

[11] Patent Number: 4,963,633

[45] Date of Patent: Oct. 16, 1990

[54] BISACRYLATE MONOMERS AND POLYMERS EXHIBITING NONLINEAR OPTICAL RESPONSE

[75] Inventors: Ronald N. DeMartino, Wayne; Anthony J. East, Madison; Gordon W. Calundann, North Plainfield, all of N.J.

[73] Assignee: Hoechst Celanese Corp., Somerville, N.J.

[21] Appl. No.: 434,261

[22] Filed: Nov. 13, 1989

Related U.S. Application Data

[62] Division of Ser. No. 135,764, Dec. 21, 1987, Pat. No. 4,922,003.

[51] Int. Cl.[5] .................. C08F 20/10; C08F 120/10
[52] U.S. Cl. ............................. 526/323.2; 526/326; 526/323.1; 252/299.01; 560/221
[58] Field of Search .............. 526/323.2, 323.1, 326; 252/299.01

[56] References Cited

U.S. PATENT DOCUMENTS 4,613,619  9/1986  Sleigh et al. .................. 560/221

FOREIGN PATENT DOCUMENTS 0321891  6/1989  European Pat. Off. .
7040448  3/1982  Japan .
8170737  10/1983  Japan .
3290857  11/1988  Japan .

Primary Examiner—Paul J. Killos
Attorney, Agent, or Firm—DePaoli & O'Brien

[57] ABSTRACT

This invention provides novel bisacrylate monomers and thermoset polymers which exhibit nonlinear optical response. The polymers have utility as a transparent nonlinear optical component in optical light switch and light modulator devices.

An invention bisacrylate monomer is illustrated by the following structure:

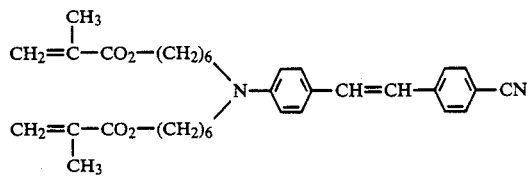

5 Claims, No Drawings

BISACRYLATE MONOMERS AND POLYMERS EXHIBITING NONLINEAR OPTICAL RESPONSE

This application is a division, of application Ser. No. 135,764, filed Dec. 21, 1987 now U.S. Pat. No. 4,922,003.

CROSS-REFERENCES TO RELATED APPLICATIONS

The subject matter of this patent application is related to that disclosed in patent application Ser. No. 822,094, filed Jan. 24, 1986; patent application Ser. No. 915,179, filed Oct. 3, 1986; patent application Ser. No. 106,301, filed Oct. 9, 1987; patent application Ser. No. 121,302 filed Nov. 10, 1987, now U.S. Pat. No. 4,801,670 and patent application Ser. No. 120,253 filed Nov. 10, 1987, now U.S. Pat. No. 4,822,865.

BACKGROUND OF THE INVENTION

It is known that organic and polymeric materials with large delocalized $\pi$-electron systems can exhibit nonlinear optical response, which in many cases is a much larger response than by inorganic substrates.

In addition, the properties of organic and polymeric materials can be varied to optimize other desirable properties, such as mechanical and thermoxidative stability and high laser damage threshold, with preservation of the electronic interactions responsible for nonlinear optical effects.

Thin films of organic or polymeric materials with large second order nonlinearities in combination with silicon-based electronic circuitry have potential as systems for laser modulation and deflection, information control in optical circuitry, and the like.

Other novel processes occurring through third order nonlinearity such as degenerate four-wave mixing, whereby real-time processing of optical fields occurs, have potential utility in such diverse fields as optical communications and integrated circuit fabrication.

Of particular importance for conjugated organic systems is the fact that the origin of the nonlinear effects is the polarization of the $\pi$-electron cloud as opposed to displacement or rearrangement of nuclear coordinates found in inorganic materials.

Nonlinear optical properties of organic and polymeric materials was the subject of a symposium sponsored by the ACS division of Polymer Chemistry at the 18th meeting of the American Chemical Society, September 1982. Papers presented at the meeting are published in ACS Symposium Series 233, American Chemical Society, Washington, D.C. 1983.

The above recited publications are incorporated herein by reference.

Of more specific interest with respect to the present invention embodiments is prior art relating to polymers with comb-like side chains. Eur. Polym. J., 18, 651(1982) describes liquid crystalline polymers of the smectic and nematic types with cyanobiphenyl groups in the side chain:

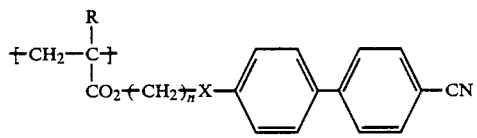

where R is hydrogen or methyl, n is an integer of 2-11, and X is an oxy, alkylene or carbonyloxy divalent radical.

A disadvantage of liquid crystalline polymers which exhibit mesogenic side chain nonlinear optical response is an observed light scattering effect when the polymer is in the form of a solid phase optical medium, e.g., the polymer medium exhibits more than about 20 percent scattering of transmitted incident light. The light scattering is due to deviations from ideal molecular order which accommodate defects that are not optically clear.

There is continuing interest in the theory and practice of polymers which are characterized by comb-like side chain structures which can be oriented in an applied external field.

There is also an increasing research effort to develop new nonlinear optical organic systems for prospective novel phenomena and devices adapted for laser frequency conversion, information control in optical circuitry, light valves and optical switches. The potential utility of organic materials with large second order and third order nonlinearities for very high frequency application contrasts with bandwidth limitations of conventional inorganic electrooptic materials.

Accordingly, it is an object of this invention to provide a novel class of bisacrylate monomers.

It is another object of this invention to provide bisacrylate polymers having side chains which exhibit nonlinear optical response.

It is a further object of this invention to provide an optically transparent medium of a thermoset bisacrylate polymer which exhibits second order nonlinear optical response.

Other objects and advantages of the present invention shall become apparent from the accompanying description and examples.

DESCRIPTION OF THE INVENTION

One or more objects of the present invention are accomplished by the provision of a bisacrylate composition corresponding to the formula:

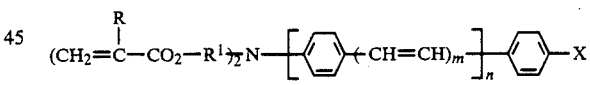

where R is a $C_1$–$C_4$ alkyl substituent, $R^1$ is a divalent $C_2$–$C_{12}$ alkylene radical, m is an integer with a value of 0–2, n is an integer with a value of 0–1, and X is an electron-withdrawing substituent.

Illustrative of $C_2$–$C_4$ alkyl substituents in the above bisacrylate formula are methyl, ethyl, propyl, isopropyl, butyl, isobutyl, and the like.

Illustrative of $C_2$–$C_{12}$ alkylene radicals are divalent substituents such as ethylene, 1,2-propylene, 1,4-butylene, 1,2-hexylene, 1,6-hexylene, 1,8-octylene, 1,10-decylene, and the like.

Illustrative of electron-withdrawing groups as represented by X in the above formula are nitro, cyano, trifluoromethyl, acyl, carboxy, alkanoyloxy, aroyloxy, carboxamido, alkoxysulfonyl, aryloxysulfonyl, and the like.

In another embodiment this invention provides a process for producing a thermoset polymer product which comprises polymerizing a monomer corresponding to the formula:

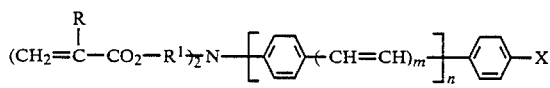

where R is a $C_1$–$C_4$ alkyl substituent, $R^1$ is a divalent $C_2$–$C_{12}$ alkylene radical, m is an integer with a value of 0–2, n is an integer with a value of 0–1, and X is an electron-withdrawing substituent.

The polymerization can be effected by heat treatment, initiation with a catalyst or irradiation with an energy source such as ultraviolet light, or by a combination of the methods.

Suitable catalysts are illustrated by free radical acid, azobiscyclohexanecarbonitrile, azobisisobutyronitrile, and the like.

A present invention bisacrylate polymer can contain other vinyl comonomeric units in addition to the acrylate units. Illustrative of copolymerizable vinyl monomers are vinyl halide, vinyl carboxylate, acrylonitrile, methacrylonitrile, alkene, arylvinyl, and the like. Suitable vinyl monomers include vinyl chloride, vinyl acetate, ethylene, propylene, isobutylene, isoprene and styrene.

The additional vinyl comonomer or comonomers can be incorporated in a proportion up to about 30 mole percent of a present invention copolymer.

A present invention thermoset bisacrylate polymer or copolymer has a glass-like appearance which is optically transparent. The thermoset polymer can be in the form of a film, coating on a substrate, molded structure, or the like.

The thermoset polymer medium can exhibit third order nonlinear optical susceptibility $\chi^{(3)}$, or second order nonlinear optical susceptibility $\chi^{(2)}$, as more fully described hereinafter.

The term "transparent" as employed herein refers to an optical medium which is transparent or light transmitting with respect to incident fundamental light frequencies and created light frequencies. In a nonlinear optical device, a present invention polymer which is incorporated as a nonlinear optical component is transparent to both the incident and exit light frequencies, and the polymeric nonlinear optical component can exhibit less than about 15 percent scattering of transmitted incident light.

In another embodiment this invention provides a process for producing a nonlinear optical medium which comprises heating and forming a melt phase medium of a bisacrylate composition corresponding to the formula:

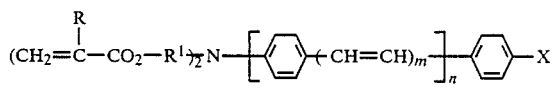

where R is a $C_1$–$C_4$ alkyl substituent, $R^1$ is a divalent $C_2$–$C_{12}$ alkylene radical, m is an integer with a value of 0–2, n is an integer with a value of 0–1, and X is an electron-withdrawing substituent; subjecting the melt phase to an external field to induce an orientation of aligned molecules in the medium, and forming a solid phase of the molecularly oriented medium while maintaining the external field effect to freeze the molecular orientation in the formed solid phase.

In the above process embodiment, the solid phase can be formed by cooling of the melt phase, or by polymerization in the melt phase after molecular orientation is induced.

If the solid phase is formed by cooling of the melt phase after molecular orientation, then the molecularly oriented solid phase can be polymerized to a thermoset medium by irradiation or catalysis means as previously described.

Synthesis Of Bisacrylate Monomers and Polymers

The preparation of bisacrylate monomers and polymers with nonlinear optically responsive side chains is illustrated by the following flow diagram:

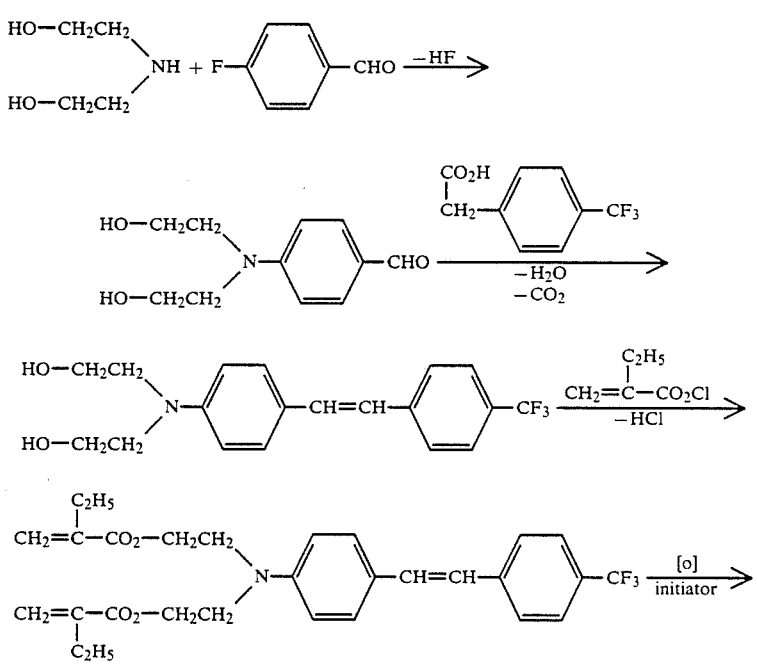

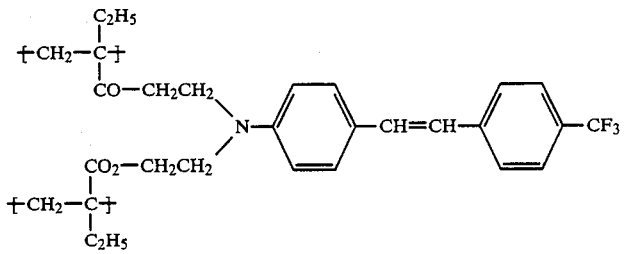

Nonlinear Optical Properties

The fundamental concepts of nonlinear optics and their relationship to chemical structures can be expressed in terms of dipolar approximation with respect to the polarization induced in an atom or molecule by an external field.

As summarized in the ACS Symposium Series 233(1983) listed hereinabove in the Background Of The Invention section, the fundamental equation (1) below describes the change in dipole moment between the ground state $\mu_g$ and an excited state $\mu_e$ expressed as a power series of the electric field E which occurs upon interaction of such a field, as in the electric component of electromagnetic radiation, with a single molecule. The coefficient $\alpha$ is the familiar linear polarizability, $\beta$ and $\gamma$ are the quadratic and cubic hyperpolarizabilities, respectively. The coefficients for these hyperpolarizabilities are tensor quantities and therefore highly symmetry dependent. Odd order coefficients are nonvanishing for all structures on the molecular and unit cell level. The even order coefficients such as $\beta$ are zero for those structures having a center of inversion symmetry on the molecular and/or unit cell level.

Equation (2) is identical with (1) except that it describes a macroscopic polarization, such as that arising from an array of molecules in a polymer domain:

$$\Delta\mu = \mu_e - \mu_g = \alpha E + \beta EE + \gamma EEE + \ldots \quad (1)$$

$$P = P_O + \chi^{(1)}E + \chi^{(2)}EE + \chi^{(3)}EEE + \ldots \quad (2)$$

Light waves passing through an array of molecules can interact with them to produce new waves. This interaction may be interpreted as resulting from a modulation in refractive index or alternatively as a nonlinearity of the polarization. Such interaction occurs most efficiently when certain phase matching conditions are met, requiring identical propagation speeds of the fundamental wave and the harmonic wave. Birefringent crystals often possess propagation directions in which the refractive index for the fundamental $\omega$ and the second harmonic $2\omega$ are identical so that dispersion may be overcome.

The term "phase matching" as employed herein refers to an effect in a nonlinear optical medium in which a harmonic wave is propagated with the same effective refractive index as the incident fundamental light wave Efficient second harmonic generation requires a nonlinear optical medium to possess propagation directions in which optical medium birefringence cancels the dispersion as a function of wavelength, i.e., the optical transmission of fundamental and second harmonic frequencies is phase matched in the medium. The phase matching can provide a high conversion percentage of the incident light to the second harmonic wave.

For the general case of parametric wave mixing, the phase matching condition is expressed by the relationship:

$$n_1\omega_1 + n_2\omega_2 = n_3\omega_3$$

where $n_1$ and $n_2$ are the indexes of refraction for the incident fundamental radiation, $n_3$ is the index of refraction for the created radiation, $\omega_1$ and $\omega_2$ are the frequencies of the incident fundamental radiation and $\omega_3$ is the frequency of the created radiation. More particularly, for second harmonic generation, wherein $\omega_2$ and $\omega_2$ are the same frequency $\omega$, and $\omega_3$ is the created second harmonic frequency $2\omega$, the phase matching condition is expressed by the relationship:

$$n_\omega = n_{1\omega}$$

where $n_{1\omega}$ and $n_{2\omega}$ are indexes of refraction for the incident fundamental and created second harmonic light waves, respectively. More detailed theoretical aspects are described in "Quantum Electronics" by A. Yariv, chapters 16-17 (Wiley and Sons, New York, 1975).

A present invention bisacrylate polymer medium typically has excellent optical transparency and exhibits hyperpolarization tensor properties such as second harmonic and third harmonic generation, and the linear electrooptic (Pockels) effect. For second harmonic generation, the bulk phase of the bisacrylate polymer medium whether liquid or solid does not possess a real or orientational average inversion center. The medium is a macroscopic noncentrosymmetric structure.

Harmonic generation measurements relative to quartz can be performed to establish the value of second order and third order nonlinear susceptibility of the optically clear substrates.

In the case of macroscopic nonlinear optical media that are composed of noncentrosymmetric sites on the molecular and domain level, the macroscopic second order nonlinear optical response $\chi^{(2)}$ is comprised of the corresponding molecular nonlinear optical response $\beta$. In the rigid lattice gas approximation, the macroscopic susceptibility $\chi^{(2)}$ is expressed by the following relationship:

$$\chi_{ijk}(-\omega_3; \omega_1,\omega_2) = Nf^{\omega_3}f^{\omega_2}f^{\omega_1} <\beta_{ijk}(-\omega_3; \omega_1,\omega_2)>$$

wherein N is the number of sites per unit volume, f represent small local field correlations, $\beta_{ijk}$ is averaged over the unit cell, $\omega_3$ is the frequency of the created optical wave, and $\omega_2$ and $\omega_2$ the frequencies of the incident fundamental optical waves.

A nonlinear optical medium with a centrosymmetric configuration of polymer molecules as defined herein can exhibit third order nonlinear optical susceptibility $\chi^{(3)}$ of at least about $1 \times 10^{-3}$ esu as measured at 1.91 μm excitation wavelength.

A nonlinear optical medium with an external field-induced noncentrosymmetric configuration of polymer molecules as defined herein can exhibit second order nonlinear optical susceptibility $\chi^{(2)}$ of at least about $1.0 \times 10^{-8}$ esu as measured at 1.91 μm excitation wavelength.

These theoretical considerations are elaborated by Garito et al in chapter 1 of the ACS Symposium Series 233 (1983); and by Lipscomb et al in J. Chem., Phys., 75, 1509 (1981), incorporated by reference. See also Lalama et al, Phys Rev., A20, 1179 (1979); and Garito et al, Mol Cryst and Liq. Cryst., 106, 219 (1984); incorporated by reference.

External Field-Induced Side Chain Orientation

The term "external field" as employed herein refers to an electric, magnetic or mechanical stress field which is applied to a medium of mobile organic molecules, to induce dipolar alignment of the molecules parallel to the field.

The nonlinear optically responsive bisacrylate monomers of the present invention may be aligned by the application of an external field to a mobile matrix of the monomer molecules. Application of a DC electric field produces orientation by torque due to the interaction of the applied electric field and the net molecular dipole moment of the monomer structure. The molecular dipole moment is due to both the permanent dipole moment (i.e., the separation of fixed positive and negative charge and the induced dipole moment (i.e., the separation of positive and negative charge by the applied field).

Application of an AC electric field also can induce bulk alignment. In this case, orienting torque occurs solely due to the interaction of the applied AC field and the induced dipole moment. Typically, AC field strengths exceeding 1 kV/cm at a frequency exceeding 1 KHz are employed.

Application of a magnetic field also can effect alignment. Organic molecules do not possess a permanent magnetic dipole moment. In a manner analogous to AC electric field, a magnetic field can induce a net magnetic dipole moment. Torque results from the interaction of the induced dipole moment and the external magnetic field. Magnetic field strengths exceeding 10 Kgauss are sufficient to induce alignment of mobile bisacrylate monomer molecules.

Mechanical stress induced molecular alignment is applicable to bisacrylate monomers Specific mechanical stress methods include stretching a thin film, or coating the surface of a bisacrylate monomer or its partially polymerized form with an aligning polymer such as nylon. Physical methods (e.g., stretching) rely upon the rigid and geometrically asymmetric character of the bisacrylate molecules to induce bulk orientation. Chemical methods (e.g., coating the surface with an aligning polymer) rely upon strong intermolecular interactions to induce surfaqe orientation.

Application of an AC electric, magnetic or mechanical external field produces colinear molecular alignment in which the molecular direction (either parallel or antiparallel to the orientation axis) is statistically random, and the resultant molecularly oriented medium exhibits third order nonlinear optical susceptibility $\chi^{(3)}$. Application of a DC electric external field produces colinear molecular alignment in which the molecular direction is not random, and is characterized by a net parallel alignment of molecular dipoles. The resultant molecularly oriented medium exhibits second order nonlinear optical susceptibility $\chi^{(2)}$.

The orientation of the bisacrylate monomer is accomplished when the monomer molecules are in a mobile phase, e.g., the monomer is at a temperature near or above the monomer melting point. The aligned phase of the mobile molecules can be frozen by cooling the medium while the aligned phase is still under the influence of the applied external field.

The following examples are further illustrative of the present invention. The components and specific ingredients are presented as being typical, and various modifications can be derived in view of the foregoing disclosure within the scope of the invention.

EXAMPLE I

This Example illustrates the preparation of bisacrylate monomers in accordance with the present invention.

A. 4-Nitrophenylimino-bis-ethanol

A one liter 4-neck flask fitted with a sealed glass paddle stirrer, inert gas inlet, reflux condenser with gas bubbler on top, and pressure-equalizing additional funnel is charged with 315 g (3.0 moles) of diethanolamine. The system is sparged with argon, and the flask is heated with stirring to 150° C. in a thermostat-controlled oil bath. A 141 g (1.0 mole) quantity of 1-fluoro-4-nitrobenzene is added dropwise from the addition funnel under argon with stirring. When all the nitrofluorobenzene has been added, the flask is stirred two more hours at 150° C. and allowed to stand at room temperature for about 20 hours. The resultant viscous product mixture is warmed and added with vigorous stirring to 3 liters of water to form a slurry of a bright yellow crystalline solid. The slurry is filtered, and the recovered solid is dried in a vacuum oven. The yield of crude product is 224 g (99% of theory).

The crude product is dissolved in one liter of hot ethanol, and a crystalline product is obtained by cooling at −15° C. The crystalline product is recovered by filtration, washed, and dried in a vacuum oven to provide 167 g (74%) of yellow product, mp 103°–105° C.

The pure product gives one spot on a thin layer silica-gel chromatoplate, Rf 0.26 in ethyl acetate. Infrared spectrum indicates a broad OH band around 3300 cm$^{-1}$.

B. 4-Nitrophenylimino-bis-(2'-ethyl acrylate)

A one liter flask fitted with an inverted-type Dean-Stark water separator tube and reflux condenser is charged with 22.6 (0.10 mole) of 4-nitrophenylimino-bis-ethanol, 10.6 g (0.10 mole) of methanesulfonic acid, 36 g (0.50 mole) of glacial acrylic acid, 1.5 g of 4-methoxyphenol as an inhibitor and 500 ml of chloroform. The mixture is refluxed with stirring until no more water collects in the Dean-Stark tube (2-3 days). A total of 4.0 ml (theory 3.6 ml) of water is collected.

The yellow chloroform solution is cooled and shaken with a solution of 60 g of anhydrous sodium carbonate in 650 ml of water to remove acidic material, then washed with water twice and dried over anhydrous magnesium sulfate. Removal of the solvent provides a yellow oil which crystallizes on standing. The solid is rectystallized from 200 ml of hot ethanol to give lemon-yellow prisms, m.p. 83-85° C., 25.6 g (76% of theory).

The infrared spectrum of the product indicates ester carbonyl absorption at 1715 cm$^{-1}$ and no OH bands. Proton NMR spectroscopy confirms the identity of the product as the bisacrylate. The compound gives one spot Rf 0.87 in ethyl acetate on a silica-gel plate, while the starting material has Rf 0.26.

C. 4-Nitrophenylimino-bis-(2'-ethyl methacrylate)

Following the above described procedures, bismethacrylate product is prepared from 22.6 g (0.10 mole) of 4-nitrophenyl-imino-bis-ethanol, 43 g (0.50 mole) of methacrylic acid, 11.0 g (0.114 mole) of methanesulfonic acid, 1.0 g of 4-methoxyphenol, and 500 ml of chloroform. After 24 hours of reaction time, the chloroform solution of reaction product is shaken with 70 g of anhydrous sodium carbonate in 500 ml of water, then washed with water and dried over magnesium sulfate. Evaporation of the solvent provides a thick oil which crystallizes on standing. The crude product yield is 30 g (83% of theory). Recrystallization of the crude product from hot ethanol gives yellow plates, m.p. 94–96° 96° C., 15.4 g (43% theory).

TLC shows a single spot Rf 0.97 in ethyl acetate and one spot Rf 0.19 in chloroform The infrared spectrum indicates ester carbonyl at 1720 cm$^{-1}$ and no sign of OH bands. Proton NMR confirms the bismethacrylate structure.

A 50/50 mixture of the bisacrylate and bismethacrylate esters as reported above melts at 78°–83° C.

The corresponding diphenylene bismethacrylate is obtained when 4-fluoro-4'-nitrobiphenyl is substituted for 1-fluoro-4-nitrobenzene.

D. 4-Nitrostilbene-4'-imino-bis(4'-butyl acrylate)

Following the above described procedures, 4-fluoro-4'-nitrostilbene is reacted with dibutanolamine to form 4-nitrostilbene-4'-imino-bis-butanol.

This intermediate bisbutanol then is reacted with glacial acrylic acid to provide the corresponding bisacrylate product.

EXAMPLE II

This Example illustrates the preparation of thermoset polymers in accordance with the present invention.

A two gram sample of each of the four monomers described in Example I, respectively, is melted at 100°–110° C. in a test tube under argon. A trace of azobiscyclohexanecarbonitrile is added, and the melt is agitated by passage of argon gas through the melt. Within about 5 minutes the medium changes to a clear orange-colored polymeric glass.

Each polymeric glass medium is centrosymmetric in molecular configuration, and exhibits third order nonlinear optical susceptibility $\chi^{(3)}$.

EXAMPLE III

This Example illustrates a poling procedure for producing a transparent film of a bisacrylate polymer which exhibits second order nonlinear optical response in accordance with the present invention.

A. Poling Cell Construction

A poling cell is constructed from electrically conductive glass plates, such as Corning Glass EC-2301. The glass plates are washed with sulfuric acid, isopropanol, 1-dodecanol, and isopropanol, with a distilled water rinse between each washing step.

The poling cell is a sandwich type cell in which the conductive glass surfaces are in facing proximity and are separated by a polyimide film of approximately 25 micrometer thickness. A thin layer of epoxy adhesive is applied on the surfaces of the polyimide film to hold the glass plates.

After the epoxy is completely cured, the cell is washed with isopropanol and rinsed with distilled water. After drying, the cell is stored in a dry box.

B. Filling The Poling Cell

4-Nitrophenylimino-bis-(2'-ethyl acrylate) containing a trace of azobiscyclohexanecarbonitrile is melted and introduced into the space between the glass plates by charging a drop of the polymer melt to one of the openings of the poling cell space and placing the cell assembly in a vacuum oven maintained at a temperature of approximately 100° C.

C. Electric Field-Induced Orientation

Two lead wires are attached to each of the conductive glass surfaces using electrically conductive epoxy adhesive. The poling assembly is placed in a microscope hot stage (Mettler FP-82 with FP-80 Central Processor), and the sample is observed with a polarizing microscope (Leitz Ortholux Pol) for alignment.

The microscope is switched into a photodiode (Mettler Photometer No. 17517) to record the change of light intensity upon application of an electric field. The two lead wires are connected to a DC voltage source (Kepco OPS-3500).

The poling cell first is heated to 100° C. to bring the bisacrylate monomer to the melt phase. The DC voltage source is set at 2000 V. The power to the poling cell is turned on to apply an electric field across the monomer sample. The field strength is calculated to be approximately $8 \times 10^5$ V/cm. About three seconds after the electric field is applied, the photodiode signal drops close to the baseline, indicating that orientation development induced by the electric field is completed. After 30 minutes at 120° C. to polymerize the monomer, the cell is cooled to room temperature, and the poling assembly is disconnected from the power source.

When the poling assembly is removed from the microscope hot stage, by visual observation the bisacrylate polymer in the cell space is transparent. This is an indication that the molecular orientation is uniform and homogeneous throughout the sample. The polymer matrix possesses a net alignment of pendant side chain dipoles along the electric field. Parallel alignment of molecular dipoles produces macroscopic noncentrosymmetry so that the polymer exhibits second order nonlinear optical susceptibility $\chi^{(2)}$.

The procedure is repeated with 4-nitrophenylimino-bis(2'-ethyl methacrylate), except that no polymerization initiator is employed. After molecular orientation of the monomer is completed, the melt phase is cooled. The transparent film of solid-phase oriented monomer in the cell is polymerized by exposing the film to ultraviolet radiation for two hours. The resultant polymer medium exhibits second order nonlinear optical response.

What is claimed is:

1. A process for producing a nonlinear optical medium which comprises heating and forming a melt phase medium of a bisacrylate composition corresponding to the formula:

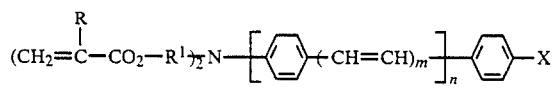

where R is a $C_1$-$C_4$ alkyl substituent, $R^1$ is a divalent $C_2$-$C_{12}$ alkylene radical, m is an integer with a value of 0–2, n is an integer with a value of 0–1, and X is an electron-withdrawing substituent; subjecting the melt phase to an external field to induce an orientation of aligned molecules in the medium, and forming a solid phase of the molecularly oriented medium while maintaining the external field effect to freeze the molecular orientation in the formed solid phase.

2. A process in accordance with claim 1, wherein the solid phase is formed by cooling of the melt phase.

3. A process in accordance with claim 1 wherein polymerization of the bisacrylate occurs in the melt phase after molecular orientation is induced.

4. A process in accordance with claim 1 wherein polymerization of the bisacrylate occurs in the molecularly oriented solid phase.

5. A nonlinear optical medium produced in accordance with the process of claim 1.

* * * * *